US006248584B1

(12) United States Patent
Cahoon et al.

(10) Patent No.: US 6,248,584 B1
(45) Date of Patent: Jun. 19, 2001

(54) TRANSCRIPTION COACTIVATORS

(75) Inventors: Rebecca E. Cahoon, Wilmington, DE (US); Joan T. Odell, Unionville, PA (US); J. Antoni Rafalski, Wilmington, DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/342,648

(22) Filed: Jun. 29, 1999

Related U.S. Application Data

(60) Provisional application No. 60/092,659, filed on Jul. 13, 1998.

(51) Int. Cl.[7] ............................. C12N 5/00; C07H 21/02; C07K 14/00
(52) U.S. Cl. .................. 435/325; 435/252.3; 435/320.1; 536/23.1; 530/350
(58) Field of Search ................................ 435/69.1, 320.1, 435/252.3, 325; 536/23.1; 530/350

(56) References Cited

FOREIGN PATENT DOCUMENTS

| 2150039 | 5/1995 | (CA) | ............................. A01H/1/00 |
|---|---|---|---|
| 0 475 584 A2 | 3/1992 | (EP) | ............................. C12N/15/29 |
| 0 589 841 A2 | 3/1994 | (EP) | ............................. C12N/15/82 |
| WO 93/10250 | 5/1993 | (WO) | ............................. C12N/15/81 |
| WO 99/04004 | 1/1999 | (WO) | ............................. C12N/15/29 |

OTHER PUBLICATIONS

Uchimiya, H., On nucleotide sequence of Oryza sativa—unpublished, *EMBL Sequence Data Library*, XP002127117, May 5, 1998.

Berger et al, Genetic isolation of ADA2: a potential transcriptional adaptor required for function of certain acidic activation domains, *Cell*, 70, 251–265, 1992.

Ma et al, Yeast activators stimulate plant gene expression, *Nature*, 334, 631–633, Aug. 18, 1988.

Bevan et al, Analysis of 1.9 Mb of contiguous sequence from chromosome 4 of *Arabidopsis thaliana*, *Nature*, 391, 485–488, Jan. 29, 1998.

Triezenberg et al., Gene Dev. 2:718–729 (1988).

Lin et al., Nature 353:569–571 (1991).

Stringer et al., Nature 345:783–786, (1990).

Xiao et al., Mol. Cell. Biol. 14:7013–7024, (1994).

Biochem. Biophys. Res. Commun., 254(3), pp. 605–613 (1999).

Tong et al., Mol. Cell Biol., 15(9), pp. 4735–4744 (1995).

Berger et al., 1990, Cell, 61:1199–1208.

Pugh and Tjian, 1990, Cell, 61:1187–1197.

Kelleher et al., 1990, Cell, 61:1209–1215.

Tong et al., (1995), Mol. Cell. Biol. 15(9):4735–4744.

Biochem. Biophys. Res. Commun. 254(3), 605–613, (1999).

*Primary Examiner*—Karen Cochrane Carlson

(57) ABSTRACT

This invention relates to an isolated nucleic acid fragment encoding a transcription coactivator. The invention also relates to the construction of a chimeric gene encoding all or a portion of the transcription coactivator, in sense or antisense orientation, wherein expression of the chimeric gene results in production of altered levels of the transcription coactivator in a transformed host cell.

13 Claims, No Drawings

TRANSCRIPTION COACTIVATORS

This application claims the benefit of U.S. Provisional Application No. 60/092,659, filed Jul. 13, 1998.

FIELD OF THE INVENTION

This invention is in the field of plant molecular biology. More specifically, this invention pertains to nucleic acid fragments encoding transcription coactivators in plants and seeds.

BACKGROUND OF THE INVENTION

In eukaryotes transcription initiation requires the action of several proteins acting in concert to initiate mRNA production. Two cis-acting regions of DNA have been identified that bind transcription initiation proteins. The first binding site located approximately 25–30 bp upstream of the transcription initiation site is termed the TATA box. The second region of DNA required for transcription initiation is the upstream activation site (UAS) or enhancer region. This region of DNA is somewhat distal from the TATA box. During transcription initiation RNA polymerase II is directed to the TATA box by general transcription factors. Transcription activators which have both a DNA binding domain and an activation domain bind to the UAS region and stimulate transcription initiation by physically interacting with the general transcription factors and RNA polymerase. Direct physical interactions have been demonstrated between activators and general transcription factors in vitro, such as between the acidic activation domain of herpes simplex virus VP16 and TATA-binding protein (TBP), TFIIB, or TFIIH (Triezenberg et al. (1988) *Gene Dev.* 2:718–729; Stringer et al. (1990) *Nature* 345:783–786; Lin et al. (1991) *Nature* 353:569–571; Xiao et al. (1994) *Mol. Cell. Biol.* 14:7013–7024).

A third factor that is involved in the interaction is the adaptor proteins. It is thought that adaptor proteins serve to mediate the interaction between transcriptional activators and general transcription factors. Functional and physical interactions have also been demonstrated between the activators and various transcription adaptors or coactivators. These transcription coactivators normally cannot bind to DNA directly, however they can "bridge" the interaction between transcription activators and general transcription factors (Pugh and Tjian (1990) *Cell* 61:1187–1197; Kelleher et al. (1990) *Cell* 61:1209–1215; Berger et al. (1990) *Cell* 61:1199–1208).

In humans Epstein-Barr virus nuclear antigen 2 (EBNA 2) activates transcription of specific genes essential for B-lymphocyte transformation. EBNA 2 has an acidic activation domain which interacts with general transcription factors TFIIB, TFIIH, and TAF40. It has been shown that EBNA 2 is specifically bound to a novel nuclear protein, p100, and that p100 can coactivate gene expression mediated by the EBNA 2 acidic domain. Interestingly, p100 also appears to be essential for normal cell growth, since it has been shown that cell viability is reduced by antisense p100 RNA and restored by sense p100 RNA expression (Tong et al., (1995) *Mol. Cell Biol.*15(9):4735–4744).

Accordingly, the availability of nucleic acid sequences encoding all or a portion of ALY transcription coactivator proteins would facilitate studies to better understand transcription in plants and ultimately provide methods to engineer mechanisms to control transcription.

SUMMARY OF THE INVENTION

The instant invention relates to isolated nucleic acid fragments encoding transcription coactivators. Specifically, this invention concerns an isolated nucleic acid fragment encoding a P100 transcription coactivator and an isolated nucleic acid fragment that is substantially similar to an isolated nucleic acid fragment encoding a P100 transcription coactivator. In addition, this invention relates to a nucleic acid fragment that is complementary to the nucleic acid fragment encoding P100.

An additional embodiment of the instant invention pertains to a polypeptide encoding all or a substantial portion of a P100 transcription coactivator.

In another embodiment, the instant invention relates to a chimeric gene encoding a P100 transcription coactivator, or to a chimeric gene that comprises a nucleic acid fragment that is complementary to a nucleic acid fragment encoding a P100 transcription coactivator, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a P100 transcription coactivator, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a P100 transcription coactivator in a transformed host cell comprising: a) transforming a host cell with a chimeric gene comprising a nucleic acid fragment encoding a P100 transcription coactivator; and b) growing the transformed host cell under conditions that are suitable for expression of the chimeric gene wherein expression of the chimeric gene results in production of altered levels of P100 in the transformed host cell.

An addition embodiment of the instant invention concerns a method for obtaining a nucleic acid fragment encoding all or a substantial portion of an amino acid sequence encoding a P100 transcription coactivator.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Transcription Coactivators

| Protein | Clone Designation | SEQ ID NO: (Nucleotide) | SEQ ID NO: (Amino Acid) |
|---|---|---|---|
| P100 | Contig composed of: | 1 | 2 |
|  | p0079.ctxme60r |  |  |
|  | p0119.cmtng79r |  |  |
|  | p0119.cmtnr54r |  |  |
|  | p0125.czaay64r |  |  |
| P100 | Contig composed of: | 3 | 4 |
|  | rca1c.pk005.i19 |  |  |
|  | rca1n.pk031.h24 |  |  |
| P100 | Contig composed of: | 5 | 6 |
|  | sdp3c.pk011.b23 |  |  |
|  | sdp3c.pk019.h1 |  |  |
|  | se1.pk0045.a4 |  |  |
|  | sr1.pk0006.c7 |  |  |
|  | ss11c.pk001.i10 |  |  |
|  | ssm.pk0068.c2 |  |  |
| P100 | Contig composed of: | 7 | 8 |
|  | wr1.pk0030.f12 |  |  |
|  | wr1.pk148.c6 |  |  |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several P100 transcription coactivators have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other P100 transcription coactivators, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) Techniques 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at than normal or in cell types or developmental stages in which they are not normally found. This would have the effect of altering the level of transcription in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded transcription coactivator. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
| --- | --- | --- |
| p0079 | Corn whole kernel 18 days after pollination* | p0079.ctxme60r |
| p0119 | Corn ear shoot/w husk night harvested: V-12 stage* | p0119.cmtng79r p0119.cmtnr54r |
| p0125 | Corn, anther: prophase I* | p0125.czaay64r |
| rca1c | Rice nipponbare callus | rca1c.pk005.i19 rca1n.pk031.h24 |
| sdp3c | Soybean developing pods 8–9 mm | sdp3c.pk011.b23 sdp3c.pk019.h1 |
| se1 | Soybean embryo, 6–10 days after flowering | se1.pk0045.a4 |
| sr1 | Soybean root library | sr1.pk0006.c7 |
| ssl1c | Soybean seed 25 days after flowering | ssl1c.pk001.i10 |
| ssm | Soybean shoot meristem | ssm.pk0068.c2 |
| wr1 | Wheat root; 7 day od seedling, light grown | wr1.pk0030.f12 wr1.pk148.c6 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding transcription coactivators were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding P100 Transcription Coactivators

The BLASTX search using the EST sequences from clones listed in Table 3 revealed similarity of the polypeptides encoded by the cDNAs to P100 transcription coactivators from *Homo sapiens* (NCBI Identifier No. gi 799177) and *Ajellomces capsulatus* (NCBI Identifier No. gi 3135013). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Homo sapiens* and *Ajellomces capsulatus* P100 Transcription Coactivators

| Clone | Status | BLAST pLog Score |
| --- | --- | --- |
| Contig composed of: | Contig | 95.40 (gi 799177) |
| p0079.ctxme60r | | |
| p0119.cmtng79r | | |
| p0119.cmtnr54r | | |
| p0125.czaay64r | | |
| Contig composed of: | Contig | 37.40 (gi 3135013) |
| rca1c.pk005.i19 | | |
| rca1n.pk031.h24 | | |
| Contig composed of: | Contig | 80.70 (gi 799177) |
| sdp3c.pk011.b23 | | |
| sdp3c.pk019.h1 | | |
| se1.pk0045.a4 | | |
| sr1.pk0006.c7 | | |
| ssl1c.pk001.i10 | | |
| ssm.pk0068.c2 | | |
| Contig composed of: | Contig | 65.70 (gi 799177) |
| wr1.pk0030.f12 | | |
| wr1.pk148.c6 | | |

The data in Table 4 represents a calculation of the percent identity of the amino acid sequences set forth in SEQ ID NOs:2, 4, 6 and 8 and the *Homo sapiens* and *Ajellomces capsulatus* sequence (SEQ ID NO:9 and 10 respectively).

TABLE 4

Percent Identity of Amino Acid Sequences Deduced From the Nucleotide Sequences of cDNA Clones Encoding Polypeptides Homologous to *Homo sapiens* and *Ajellomces capsulatus* P100 Transcription Coactivators

| SEQ ID NO. | Percent Identity to |
| --- | --- |
| 2 | 22% (gi 799177) |
| 4 | 19% (gi 3135013) |
| 6 | 25% (gi 799177) |
| 8 | 24% (gi 799177) |

Sequence alignments and percent identity calculations were performed using the Megalign program of the LASAR- GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a P100 transcription coactivator. These sequences represent the first plant sequences encoding P100.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.*

261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated nucleic acid molecule comprising:
   (a) a nucleotide sequence encoding a P100 transcription coactivator, wherein the amino acid sequence of the coactivator is at least 80% identical to the amino acid sequence of SEQ ID NO:2, SEQ ID NO:4, SEQ ID NO:6, or SEQ ID NO:8, or
   (b) the complement of the nucleotide sequence (a).

2. The nucleic acid molecule of claim 1 being RNA.

3. The nucleic acid molecule of claim 1, wherein the amino acid sequence of the coactivator is at least 90% identical to the amino acid sequence of SEQ ID NO:2, SEQ ID NO:4, SEQ ID NO:6, or SEQ ID NO:8.

4. The nucleic acid molecule of claim 1, wherein the amino acid sequence of the coactivator is at least 95% identical to the amino acid sequence of SEQ ID NO:2, SEQ ID NO:4, SEQ ID NO:6, or SEQ ID NO:8.

5. The nucleic acid molecule of claim 1, wherein the coactivator comprises the amino acid sequence of SEQ ID NO:2, SEQ ID NO:4, SEQ ID NO:6, or SEQ ID NO:8.

6. The nucleic acid molecule of claim 1, wherein the nucleotide sequence comprises the nucleotide sequence of SEQ ID NO:1, SEQ ID NO:3, SEQ ID NO:5, or SEQ ID NO:7.

7. An expression vector comprising the nucleic acid molecule of claim 1 operably linked to regulatory sequences suitable for the expression of the nucleotide sequence.

8. An isolated P100 transcription coactivator, wherein the amino acid sequence of the coactivator is at least 80% identical to the amino acid sequence of SEQ ID NO:2, SEQ ID NO:4, SEQ ID NO:6, or SEQ ID NO:8.

9. The coactivator of claim 8, wherein the amino acid sequence of the coactivator is at least 90% identical to the amino acid sequence of SEQ ID NO:2, SEQ ID NO:4, SEQ ID NO:6, or SEQ ID NO:8.

10. The coactivator of claim 8, wherein the amino acid sequence of the coactivator is at least 95% identical to the amino acid sequence of SEQ ID NO:2, SEQ ID NO:4, SEQ ID NO:6, or SEQ ID NO:8.

11. The coactivator of claim 8 comprising the amino acid sequence of SEQ ID NO:2, SEQ ID NO:4, SEQ ID NO:6, or SEQ ID NO:8.

12. A method for transforming a cell comprising transforming a cell with the nucleic acid molecule of claim 11.

13. The cell produced by the method of claim 12.

* * * * *

SEQUENCE LISTING

```
<160> NUMBER OF SEQ ID NOS: 10

<210> SEQ ID NO 1
<211> LENGTH: 2525
<212> TYPE: DNA
<213> ORGANISM: Zea mays
<220> FEATURE:
<221> NAME/KEY: unsure
<222> LOCATION: (537)
<220> FEATURE:
<221> NAME/KEY: unsure
<222> LOCATION: (555)
<220> FEATURE:
<221> NAME/KEY: unsure
<222> LOCATION: (610)
<220> FEATURE:
<221> NAME/KEY: unsure
<222> LOCATION: (722)
<220> FEATURE:
<221> NAME/KEY: unsure
<222> LOCATION: (754)

<400> SEQUENCE: 1
ggctgaaact gatgataatg ctaatatcgc gaacgctgaa gatcctgagg gaacacctgc      60
gcaactgact acagcacaaa ggctagttgc atctgcagct tctgctgaaa ttccaccaga     120
taggtatgga agagaagcca aacatttcac agagactaga gttctcaaca gagatgtgcg     180
tattgtggtg gaaggcacag acagctttag taatataatt ggttctgtgt attaccctga     240
tggagagact gcaaaggact tggcccttga gcttgtcgaa aatgggctgg caaagtatgt     300
tgagtggagt gccaatatgc ttgatgttga agtaaaaata aagctgaaga atgcagaact     360
tcaggctaaa aaggatcaat tgagaatctg gacagggttt aagccaccag cgacaaactc     420
gaagcccatt catgaccaga aatttaatgg aaaagtggta gaggttgtaa gtggggattg     480
cattattgtg gctgatgatt ctgctccata tggcagtcct tcagccgaac gtcgggntaa     540
tctgtcaagc attanggccc ctaagttggg caatgctcgt acagatgtga agcctgacca     600
ttttgctcgn gaagctaagg agttcttgcg catgaggtta ttggcaagc aagtggctgt     660 tgaaatggaa tattctcgaa ggatcagcac cgtggatgga cagagtgttg ctccaacagc     720
anacattgct gatacaagag tattagatta tggntcagac tttctggggtt caccatcaca     780 gactgatgga gatgacatat cttctgctcc gagctctgcc agccagcctg gagttaatgc     840
tgctgaactt ttactctcac gaggctttgc taaaacatct aaacacaggg attatgagga     900 aagtcacac tattatgatg ctttattagc agctgaatca cgcgctgaga aagcaaagaa     960
aggcgtgcat tctcagaaag aatctcctgt gatgcatata acagatttaa caactgtatc    1020
tgcaaagaag gccaaagatt ttcttccctt cttgcagcgg aacagaaggc attcggccat    1080
cgttgaatat gttttttagtg gccatcggtt caaactaaca attcctaagg agacttgcag    1140
```

-continued

```
tattgccttc tcattatctg gtgttcggtg tcctggtaaa ggcgagccat actcagatga    1200
agctattgct ttgatgagga aaggatact tcaacgagat gtggagatag aggttgaagc    1260
agttgatagg acaggaacgt tcataggttc tttgtgggag tccaagacca acatgggctc    1320
tgtgcttctg gaagctggac ttgccaagct gagttcattt ggcttggata ggacctcaga    1380
tgcttatatc ctaacaagag ctgaacagtc tgcgaagcaa cagaagatta agatatggga    1440
gaactatgtc gagggtgaaa atgcttccaa tggatccaca cctgaatcta acaaaagca    1500 aattctcaag gttgttgtca cggaagttct tggtggtggg aagttttatg ttcagacaat    1560
gggtgaccag agggtggctt caattcaaca gcagcttgca tctttgaaac ttaaagatgc    1620
gccggtcatt ggtgcttta atcctgtgaa gggagagata gtcctcgcac aatttagcgt    1680
tgacaactcc tggaacagag ctatgattgt taatggacct cgttctgttg aatctccgga    1740
cgacaagttt gaagtattct atattgacta tggcaaccaa gaggtggtta cctacagtcg    1800
tttacgacct gtagacccat ctgtttcctc gtctcctgct cttgctcagc tatgcagcct    1860
tgctttcata aaagtgccca gtcttgagga tgactttggt caggaagcag cagagtatct    1920
aagtgaatgt ttgctcagta gctcaaagca ataccgggca atgatcgaag aacatgatac    1980 ttctggggg aaatcaaaag acaaggaac cggaaatgtt ctcattgtta ctcttgttga    2040
tgcggagaca gaaagtagca taaacgctac catgcttgag gaagggcttg cccggctcga    2100
aagaagcaag agatgggaca ctagggagag gaagacggct ctccagaacc tggaacagtt    2160
ccaggacaag gcaaagaagg aaaggctgcg gatttggcag tacggagatg ttgaatcgga    2220
cgaggacgag caggccccgc ctgcaaggaa gcctggaggt cgtcggtaga gactgggcag    2280
tgtaaggctg cagtctggca tgctatgaaa gttttggaca accacaaatg ttggactctg    2340
ccgggagtta tagatgagga cttactgagg ggtaccgtat ttatattcgg ttagaagaag    2400
ggaacttagc gaggcgaaat cacttttgat attccgtttt tacaggcgaa actttctctg    2460 tttttagcact tttgatattc cgttttttaca tcgcaagtta taaggttaaa aaaaaaaa    2520 aaaaa                                                                 2525
```

<210> SEQ ID NO 2
<211> LENGTH: 755
<212> TYPE: PRT
<213> ORGANISM: Zea mays
<220> FEATURE:
<221> NAME/KEY: UNSURE
<222> LOCATION: (179)
<220> FEATURE:
<221> NAME/KEY: UNSURE
<222> LOCATION: (185)
<220> FEATURE:
<221> NAME/KEY: UNSURE
<222> LOCATION: (241)

<400> SEQUENCE: 2

```
Ala Glu Thr Asp Asp Asn Ala Asn Ile Ala Asn Ala Glu Asp Pro Glu
 1               5                   10                  15

Gly Thr Pro Ala Gln Leu Thr Thr Ala Gln Arg Leu Val Ala Ser Ala
             20                  25                  30

Ala Ser Ala Glu Ile Pro Pro Asp Arg Tyr Gly Arg Glu Ala Lys His
         35                  40                  45

Phe Thr Glu Thr Arg Val Leu Asn Arg Asp Val Arg Ile Val Val Glu
     50                  55                  60

Gly Thr Asp Ser Phe Ser Asn Ile Ile Gly Ser Val Tyr Tyr Pro Asp
 65                  70                  75                  80
```

```
Gly Glu Thr Ala Lys Asp Leu Ala Leu Glu Leu Val Glu Asn Gly Leu
                85                  90                  95

Ala Lys Tyr Val Glu Trp Ser Ala Asn Met Leu Asp Val Glu Val Lys
            100                 105                 110

Ile Lys Leu Lys Asn Ala Glu Leu Gln Ala Lys Lys Asp Gln Leu Arg
            115                 120                 125

Ile Trp Thr Gly Phe Lys Pro Pro Ala Thr Asn Ser Lys Pro Ile His
130                 135                 140

Asp Gln Lys Phe Asn Gly Lys Val Val Glu Val Val Ser Gly Asp Cys
145                 150                 155                 160

Ile Ile Val Ala Asp Asp Ser Ala Pro Tyr Gly Ser Pro Ser Ala Glu
                165                 170                 175

Arg Arg Xaa Asn Leu Ser Ser Ile Xaa Ala Pro Lys Leu Gly Asn Ala
            180                 185                 190

Arg Thr Asp Val Lys Pro Asp His Phe Ala Arg Glu Ala Lys Glu Phe
            195                 200                 205

Leu Arg Met Arg Leu Ile Gly Lys Gln Val Ala Val Glu Met Glu Tyr
            210                 215                 220

Ser Arg Arg Ile Ser Thr Val Asp Gly Gln Ser Val Ala Pro Thr Ala
225                 230                 235                 240

Xaa Ile Ala Asp Thr Arg Val Leu Asp Tyr Gly Ser Asp Phe Leu Gly
                245                 250                 255

Ser Pro Ser Gln Thr Asp Gly Asp Ile Ser Ser Ala Pro Ser Ser
                260                 265                 270

Ala Ser Gln Pro Gly Val Asn Ala Ala Glu Leu Leu Leu Ser Arg Gly
            275                 280                 285

Phe Ala Lys Thr Ser Lys His Arg Asp Tyr Glu Glu Arg Ser His Tyr
            290                 295                 300

Tyr Asp Ala Leu Leu Ala Ala Glu Ser Arg Ala Glu Lys Ala Lys Lys
305                 310                 315                 320

Gly Val His Ser Gln Lys Glu Ser Pro Val Met His Ile Thr Asp Leu
                325                 330                 335

Thr Thr Val Ser Ala Lys Lys Ala Lys Asp Phe Leu Pro Phe Leu Gln
            340                 345                 350

Arg Asn Arg Arg His Ser Ala Ile Val Glu Tyr Val Phe Ser Gly His
            355                 360                 365

Arg Phe Lys Leu Thr Ile Pro Lys Glu Thr Cys Ser Ile Ala Phe Ser
            370                 375                 380

Leu Ser Gly Val Arg Cys Pro Gly Lys Gly Glu Pro Tyr Ser Asp Glu
385                 390                 395                 400

Ala Ile Ala Leu Met Arg Arg Ile Leu Gln Arg Asp Val Glu Ile
                405                 410                 415

Glu Val Glu Ala Val Asp Arg Thr Gly Thr Phe Ile Gly Ser Leu Trp
            420                 425                 430

Glu Ser Lys Thr Asn Met Gly Ser Val Leu Leu Glu Ala Gly Leu Ala
            435                 440                 445

Lys Leu Ser Ser Phe Gly Leu Asp Arg Thr Ser Asp Ala Tyr Ile Leu
            450                 455                 460

Thr Arg Ala Glu Gln Ser Ala Lys Gln Gln Lys Ile Lys Ile Trp Glu
465                 470                 475                 480

Asn Tyr Val Glu Gly Glu Asn Ala Ser Asn Gly Ser Thr Pro Glu Ser
                485                 490                 495
```

```
Lys Gln Lys Gln Ile Leu Lys Val Val Thr Glu Val Leu Gly Gly
            500                 505                 510
Gly Lys Phe Tyr Val Gln Thr Met Gly Asp Gln Arg Val Ala Ser Ile
            515                 520                 525
Gln Gln Gln Leu Ala Ser Leu Lys Leu Lys Asp Ala Pro Val Ile Gly
            530                 535                 540
Ala Phe Asn Pro Val Lys Gly Glu Ile Val Leu Ala Gln Phe Ser Val
545                 550                 555                 560
Asp Asn Ser Trp Asn Arg Ala Met Ile Val Asn Gly Pro Arg Ser Val
                565                 570                 575
Glu Ser Pro Asp Asp Lys Phe Glu Val Phe Tyr Ile Asp Tyr Gly Asn
            580                 585                 590
Gln Glu Val Val Thr Tyr Ser Arg Leu Arg Pro Val Asp Pro Ser Val
            595                 600                 605
Ser Ser Ser Pro Ala Leu Ala Gln Leu Cys Ser Leu Ala Phe Ile Lys
            610                 615                 620
Val Pro Ser Leu Glu Asp Asp Phe Gly Gln Glu Ala Ala Glu Tyr Leu
625                 630                 635                 640
Ser Glu Cys Leu Leu Ser Ser Lys Gln Tyr Arg Ala Met Ile Glu
                645                 650                 655
Glu His Asp Thr Ser Gly Gly Lys Ser Lys Gly Gln Gly Thr Gly Asn
            660                 665                 670
Val Leu Ile Val Thr Leu Val Asp Ala Glu Thr Glu Ser Ser Ile Asn
            675                 680                 685
Ala Thr Met Leu Glu Glu Gly Leu Ala Arg Leu Glu Arg Ser Lys Arg
            690                 695                 700
Trp Asp Thr Arg Glu Arg Lys Thr Ala Leu Gln Asn Leu Glu Gln Phe
705                 710                 715                 720
Gln Asp Lys Ala Lys Lys Glu Arg Leu Arg Ile Trp Gln Tyr Gly Asp
                725                 730                 735
Val Glu Ser Asp Glu Asp Glu Gln Ala Pro Pro Ala Arg Lys Pro Gly
            740                 745                 750
Gly Arg Arg
        755
```

<210> SEQ ID NO 3
<211> LENGTH: 1487
<212> TYPE: DNA
<213> ORGANISM: Oryza sativa

<400> SEQUENCE: 3

```
gttagatgcc ctggtaaaga tgagccctac tcgaacgaag ctattgcttt gatgaggagg    60
agaattctac agcgagatgt ggagatagag gttgaagcag ttgatagaac tgggacattc   120
ttaggttcct tatgggagtc caaaaccaac atggcttctg ttcttctgga ggctggtctg   180
gccaagctta gttcatttgg cttggatagg attccggatg caaatgttct aatgagggct   240
gaacagtctg caaagcagca gaaactcaag atctgggaga attatgtaga gggtgaagaa   300
gtttccaatg gatctgcatc tgaatccaaa caaaaggaaa ttctcaaggt tgttgtaact   360
gaagtccttg gtggtggaaa gttctatgtc caaacagttg gtgaccatag agtggcttcc   420
attcaacaac agcttgcatc tttaaaactt aaagatgcac ctgttattgg tgctttttaat   480
cctgtgaagg gggaaatagt tcttgctcag tttagtgctg acaactcctg gaatagagca   540
atgattgtga atggacctcg aggagctgta tcatctcaag acgacaagtt tgaagtattc   600
```

```
tacattgact atggcaacca agaagtcgtt ccttacagtc gcatacggcc tgctgaccca    660
tcaatttcct cttcgcctgc tcttgctcag ttgtgcagcc ttgccttcat aaaagtgccc    720
aacctagaag atgattttgg ccatgaagca gcagtctatc tgaatgattg cttgctcaac    780
agccaaaaac aatacagggc aatgattgaa gagcgtgata cttctggtgg aaagtccaag    840
ggacaaggca ctggaactat tctgattgtt acactggttg acgcagagac agaaaccagc    900
atcaatgcta ccatgcttga ggaagggctt gctcggcttg aaagaagcaa gagatgggat    960
actagggaga gaaaggctgc tctccagaat ctggaacagt tccaggagaa agcaaagaag   1020
gaaaggctgc agatctggca gtatggtgat gttgaatctg acgaggaaga gcaagctcca   1080
gcggctagga gaactggagg gcgtcggtag atgagagaag ctgctcaag acagcaatgg    1140 cgtcggtaag ctatcatcaa gttttggaca ccgggtcaga ctctaccggg agctttagat   1200
gaaaaacata gagaagaaa atgaggatta ccttatttat gcagttagaa cagaacttag    1260
cgaggcgaaa cttccttagt ttgagcactg ttgcttgatg ctgaactatt attccgtttt   1320
acaccgtaat gttgaggtta agatacattg tttttcccct aaacttaata atgtcgtgta   1380
cttggtgcac tgcagttctt tgtagacaca acataatacc gagagcgcag tcaattaaaa   1440
ttcaggattg aacttaaaaa aaaaaaaaaa aaaaaaaaa aaaaaag                  1487
```

<210> SEQ ID NO 4
<211> LENGTH: 369
<212> TYPE: PRT
<213> ORGANISM: Oryza sativa

<400> SEQUENCE: 4

```
Val Arg Cys Pro Gly Lys Asp Glu Pro Tyr Ser Asn Glu Ala Ile Ala
  1               5                  10                  15

Leu Met Arg Arg Arg Ile Leu Gln Arg Asp Val Glu Ile Glu Val Glu
                 20                  25                  30

Ala Val Asp Arg Thr Gly Thr Phe Leu Gly Ser Leu Trp Glu Ser Lys
             35                  40                  45

Thr Asn Met Ala Ser Val Leu Leu Glu Ala Gly Leu Ala Lys Leu Ser
         50                  55                  60

Ser Phe Gly Leu Asp Arg Ile Pro Asp Ala Asn Val Leu Met Arg Ala
 65                  70                  75                  80

Glu Gln Ser Ala Lys Gln Lys Leu Lys Ile Trp Glu Asn Tyr Val
                 85                  90                  95

Glu Gly Glu Glu Val Ser Asn Gly Ser Ala Ser Glu Ser Lys Gln Lys
                100                 105                 110

Glu Ile Leu Lys Val Val Thr Glu Val Leu Gly Gly Lys Phe
            115                 120                 125

Tyr Val Gln Thr Val Gly Asp His Arg Val Ala Ser Ile Gln Gln Gln
            130                 135                 140

Leu Ala Ser Leu Lys Leu Lys Asp Ala Pro Val Ile Gly Ala Phe Asn
145                 150                 155                 160

Pro Val Lys Gly Glu Ile Val Leu Ala Gln Phe Ser Ala Asp Asn Ser
                165                 170                 175

Trp Asn Arg Ala Met Ile Val Asn Gly Pro Arg Gly Ala Val Ser Ser
                180                 185                 190

Gln Asp Asp Lys Phe Glu Val Phe Tyr Ile Asp Tyr Gly Asn Gln Glu
            195                 200                 205

Val Val Pro Tyr Ser Arg Ile Arg Pro Ala Asp Pro Ser Ile Ser Ser
            210                 215                 220
```

```
Ser Pro Ala Leu Ala Gln Leu Cys Ser Leu Ala Phe Ile Lys Val Pro
225                 230                 235                 240

Asn Leu Glu Asp Asp Phe Gly His Glu Ala Ala Val Tyr Leu Asn Asp
            245                 250                 255

Cys Leu Leu Asn Ser Gln Lys Gln Tyr Arg Ala Met Ile Glu Glu Arg
                260                 265                 270

Asp Thr Ser Gly Gly Lys Ser Lys Gly Gln Gly Thr Gly Thr Ile Leu
        275                 280                 285

Ile Val Thr Leu Val Asp Ala Glu Thr Glu Thr Ser Ile Asn Ala Thr
290                 295                 300

Met Leu Glu Glu Gly Leu Ala Arg Leu Glu Arg Ser Lys Arg Trp Asp
305                 310                 315                 320

Thr Arg Glu Arg Lys Ala Ala Leu Gln Asn Leu Glu Gln Phe Gln Glu
                325                 330                 335

Lys Ala Lys Lys Glu Arg Leu Gln Ile Trp Gln Tyr Gly Asp Val Glu
            340                 345                 350

Ser Asp Glu Glu Glu Gln Ala Pro Ala Ala Arg Arg Thr Gly Gly Arg
        355                 360                 365

Arg
```

```
<210> SEQ ID NO 5
<211> LENGTH: 2011
<212> TYPE: DNA
<213> ORGANISM: Glycine max
<220> FEATURE:
<221> NAME/KEY: unsure
<222> LOCATION: (1047)
<220> FEATURE:
<221> NAME/KEY: unsure
<222> LOCATION: (1919)
<220> FEATURE:
<221> NAME/KEY: unsure
<222> LOCATION: (1936)
<220> FEATURE:
<221> NAME/KEY: unsure
<222> LOCATION: (1956)
<220> FEATURE:
<221> NAME/KEY: unsure
<222> LOCATION: (1977)
<220> FEATURE:
<221> NAME/KEY: unsure
<222> LOCATION: (1983)
<220> FEATURE:
<221> NAME/KEY: unsure
<222> LOCATION: (1985)

<400> SEQUENCE: 5
gacctggcat tggagcttgt ggaaaatggt tttgccaaat atgttgaatg gagtgcaaat      60
atgatggaag aagaggcaaa acggaagctg aagacttcag agcttcaggc taagaaaaac     120
aggttaaaga tttggacaaa ctatgtacca ccggcaacaa attcaaaggc aatacatgac     180
cagaatttta caggaaaggt ggttgaggtt gttagtggag attgcatcat tgttgctgat     240
gatttgattc cgtatggcag tccactagca gagcggcgag tcaaccttc aagtattagg      300 tgtccaaaag taggcaatcc tcgtagagat gaaaaaccag ctccatatgc tcgcgaagca     360
aaggagttct tgagaacacg cctcattggt cgtcaagtaa atgttcaaat ggagtattct     420
agaaaggttg gtccagcaga tggatctgcg gttccatcag gagcttctga agctagagca     480
atggattttg gatcagtatt cctacccagc accgttaagg ctgatggtga tgatgctcct     540
tcatctgttc cacctgctgg aagtcagcaa atgggggtga atgttgggga gttgatagtt     600
agccgtggct ttggaactgt cgttagacac cgtgactttg aagagagatc aaactactat     660
```

-continued

```
gatgctctcc ttactgctga atcacgtgct atttctggaa gaaagggat ccattctgcc    720 aaggattctc cagccatgca tataactgac ttgaccacag catcagcaaa gaaagccaag    780
gatttcttgc ctttccttca ccgaagtaga aaaatccctg cagttgtggg atatgtcctt    840
agtggccatc gttttaaatt gttaattcca aaagaaactt gcagcaatgc cttttcaatt    900
tctggtgtca aatgtcctgg gcccaatgag ccatattccg atgaatcaat cgctctgatg    960
aggagaaaga taatgcaaag agatgttgag atagaggttg aaaccgttga tcgaactgga   1020
acattcttgg gatccttatg ggagtcnagg accaacgtgg caattacact gctcgaagct   1080
ggtctggcaa aactccaaac atcctttggc agtgatagaa ttcctgattt tcatcttctg   1140
gagcaagctg aacaatctgc caagaagcaa aagctgagaa tttgggagaa ctatgttgaa   1200
ggggaggaag tatctaatgg tgcacctgtc gagaacaaac aacaagaagt gctcaaggtg   1260
acagtaacag aagtcttggg tggtggtaaa ttctatgttc agacagttgg agatcaaaag   1320
attgcatcca ttcagcaaca gcttgcttct ttgaacctaa aggatgctcc tgtgcttggt   1380
gctttcaatc ctaagaaggg tgatatagtc ctttgttatt ttcatgctga caaatcttgg   1440
taccgggcaa tggttgtcaa cacaccccga ggaccagttg aatcccccaa cgacttgttc   1500
gaagtattct acgtcgatta tggaaatcaa gaagtagtac cctacagtca actacggcct   1560
gttgatccat ctgtatctgc tgctcctggt attgcacaat tgtgcagcct tgcatatgtg   1620
aaggttccaa acttggaaga ggattttggc caagaagcag ctgaatattt gagcgaactc   1680
actttaaaca gtggcaaaga gtttagggcc aaggtcgagg agagagatac atctggaggg   1740
aaagcgaaag ggcagggtac tgggacagtg cttgcggtaa ctctagtagc tgtggattcg   1800
gagatcagtg ttaatgctgc catgctacag gaaggacttg ctaggctaga aaaaaggaat   1860
aggtgggacg gaaaagaaag acaacaggcc cttgacaatt tggttccgtt ccaagggggnc   1920 gaaagctccg aaccanttag gcgttggaat gtgggnatta tggaaaatat ccaagtnctg   1980
aanancaagg acaactggct cctcctgcta a                                  2011
```

<210> SEQ ID NO 6
<211> LENGTH: 622
<212> TYPE: PRT
<213> ORGANISM: Glycine max
<220> FEATURE:
<221> NAME/KEY: UNSURE
<222> LOCATION: (4)
<220> FEATURE:
<221> NAME/KEY: UNSURE
<222> LOCATION: (10)
<220> FEATURE:
<221> NAME/KEY: UNSURE
<222> LOCATION: (20)
<220> FEATURE:
<221> NAME/KEY: UNSURE
<222> LOCATION: (52)
<220> FEATURE:
<221> NAME/KEY: UNSURE
<222> LOCATION: (74)
<220> FEATURE:
<221> NAME/KEY: UNSURE
<222> LOCATION: (77)

<400> SEQUENCE: 6

Met Phe Gly Xaa Val Leu Glu Gly Val Xaa Lys Phe Thr Asn Leu Ile
 1               5                  10                  15

Gly Ser Val Xaa Tyr Pro Asp Gly Asp Ser Ala Lys Asp Leu Ala Leu
            20                  25                  30

-continued

```
Glu Leu Val Glu Asn Gly Phe Ala Lys Tyr Val Glu Trp Ser Ala Asn
         35                  40                  45

Met Met Glu Xaa Glu Ala Lys Arg Lys Leu Lys Thr Ser Glu Leu Gln
 50                  55                  60

Ala Lys Lys Asn Arg Leu Lys Ile Trp Xaa Asn Tyr Xaa Pro Pro Ala
 65                  70                  75                  80

Thr Asn Ser Lys Ala Ile His Asp Gln Asn Phe Thr Gly Lys Val Val
                 85                  90                  95

Glu Val Val Ser Gly Asp Cys Ile Ile Val Ala Asp Asp Leu Ile Pro
                100                 105                 110

Tyr Gly Ser Pro Leu Ala Glu Arg Arg Val Asn Leu Ser Ser Ile Arg
         115                 120                 125

Cys Pro Lys Val Gly Asn Pro Arg Arg Asp Glu Lys Pro Ala Pro Tyr
 130                 135                 140

Ala Arg Glu Ala Lys Glu Phe Leu Arg Thr Arg Leu Ile Gly Arg Gln
145                 150                 155                 160

Val Asn Val Gln Met Glu Tyr Ser Arg Lys Val Gly Pro Ala Asp Gly
                165                 170                 175

Ser Ala Val Pro Ser Gly Ala Ser Glu Ala Arg Ala Met Asp Phe Gly
         180                 185                 190

Ser Val Phe Leu Pro Ser Thr Val Lys Ala Asp Gly Asp Asp Ala Pro
         195                 200                 205

Ser Ser Val Pro Pro Ala Gly Ser Gln Gln Asn Gly Val Asn Val Gly
 210                 215                 220

Glu Leu Ile Val Ser Arg Gly Phe Gly Thr Val Val Arg His Arg Asp
225                 230                 235                 240

Phe Glu Glu Arg Ser Asn Tyr Tyr Asp Ala Leu Leu Thr Ala Glu Ser
                245                 250                 255

Arg Ala Ile Ser Gly Arg Lys Gly Ile His Ser Ala Lys Asp Ser Pro
         260                 265                 270

Ala Met His Ile Thr Asp Leu Thr Thr Ala Ser Ala Lys Lys Ala Lys
         275                 280                 285

Asp Phe Leu Pro Phe Leu His Arg Ser Arg Lys Ile Pro Ala Val Val
 290                 295                 300

Gly Tyr Val Leu Ser Gly His Arg Phe Lys Leu Leu Ile Pro Lys Glu
305                 310                 315                 320

Thr Cys Ser Asn Ala Phe Ser Ile Ser Gly Val Lys Cys Pro Gly Pro
                325                 330                 335

Asn Glu Pro Tyr Ser Asp Glu Ser Ile Ala Leu Met Arg Arg Lys Ile
         340                 345                 350

Met Gln Arg Asp Val Glu Ile Glu Val Glu Thr Val Asp Arg Thr Gly
         355                 360                 365

Thr Phe Leu Gly Ser Leu Trp Glu Ser Arg Thr Asn Val Ala Ile Thr
 370                 375                 380

Leu Leu Glu Ala Gly Leu Ala Lys Leu Gln Thr Ser Phe Gly Ser Asp
385                 390                 395                 400

Arg Ile Pro Asp Phe His Leu Leu Glu Gln Ala Glu Gln Ser Ala Lys
                405                 410                 415

Lys Gln Lys Leu Arg Ile Trp Glu Asn Tyr Val Glu Gly Glu Val
         420                 425                 430

Ser Asn Gly Ala Pro Val Glu Asn Lys Gln Gln Glu Val Leu Lys Val
         435                 440                 445
```

-continued

```
Thr Val Thr Glu Val Leu Gly Gly Lys Phe Tyr Val Gln Thr Val
    450                 455                 460
Gly Asp Gln Lys Ile Ala Ser Ile Gln Gln Leu Ala Ser Leu Asn
465                 470                 475                 480
Leu Lys Asp Ala Pro Val Leu Gly Ala Phe Asn Pro Lys Lys Gly Asp
                485                 490                 495
Ile Val Leu Cys Tyr Phe His Ala Asp Lys Ser Trp Tyr Arg Ala Met
                500                 505                 510
Val Val Asn Thr Pro Arg Gly Pro Val Glu Ser Pro Asn Asp Leu Phe
            515                 520                 525
Glu Val Phe Tyr Val Asp Tyr Gly Asn Gln Glu Val Val Pro Tyr Ser
        530                 535                 540
Gln Leu Arg Pro Val Asp Pro Ser Val Ser Ala Ala Pro Gly Leu Ala
545                 550                 555                 560
Gln Leu Cys Ser Leu Ala Tyr Ile Lys Ile Pro Asn Leu Glu Glu Asp
                565                 570                 575
Phe Gly Gln Glu Ala Ala Glu Tyr Leu Ser Glu Leu Thr Leu Asn Ser
                580                 585                 590
Gly Lys Glu Phe Arg Ala Lys Val Glu Glu Lys Asp Thr Ser Gly Gly
            595                 600                 605
Lys Val Lys Gly Ala Gly Asn Trp Gly Asn Pro Cys Cys Asn
        610                 615                 620
```

<210> SEQ ID NO 7
<211> LENGTH: 1626
<212> TYPE: DNA
<213> ORGANISM: Triticum aestivum
<220> FEATURE:
<221> NAME/KEY: unsure
<222> LOCATION: (1621)

<400> SEQUENCE: 7

```
gcacgaggga cagaatgctg tgcctgtaat gaactcggct gataccagag ttttggatta      60
tggttcagtt tttctaggtt cgccatcacc ggcggacgga gatgacacat cttctgctcc     120
aagcacaggc acccagccta aaattaatgt tgctgagctt ttgctctcac ggggcttcgc     180
tgagatatca aaacaccgtg actacgagga agatcacat tattttgatg ctctattagc     240
ggctcactca cgtgctgaga agcaaagaa aggaattcac tctgacaaac ttcctcctgt     300
gatgcatata accgatttaa caatggttaa ttctaagaag gccaaagatt ccttcccctt     360
cctgcagcgg aatagaaggc atactgctgt tgttgaatat gtgttcagcg gtcatcgttt     420
caaactgaca attccaaagg agacttgcag catcgctttt tcattgtctg gtgttaggtg     480
ccctggtaaa gatgagccct actcgagcga agctattgct ttgatgagga ggatgattct     540
acagcgtgat gtggagattg aggttgaaac agttgataga actggaacat tcataggttc     600
cttgtgggag tcgaagacca acgttggttc tgttcttttta gagtctggct tgggcaagct     660
tagttcattt ggcttggata ggattccaga tgctcatgtc ctcacaagag ctgaaaagtt     720
agcaaagcag cagaaactga agatatggga gaactacgtc gagggtgaag aagttactaa     780
tgggtcagcc tctgaatcca aacaaaagga aattctcaag gttgttgcta ctgaagttct     840
tggtggtgga aagttctatg cccagacagt aggtgaccag agagtagctt ccatccaaca     900
acagcttgca tccttgaaac ttaaggaggc accagtcatt ggtgcttta atcctgggaa     960
gggagagata gttcttgctc agtttagcct cgacaactct tggaatagag ccatgattgt    1020
taatggaccc cgaggagctg tagagtctgt agatgacaaa tttgaagtat tctacattga    1080
```

-continued

```
ttttggtaac caagaagtgg ttccttacaa ccgcatccgg cctgcagacc catcagtatc    1140
ctcctctcct cctcttgctc agctgtgcag ccttgccttc atcaaagtgc ctggtctgga    1200
agatgataat ggtcaggaag cagcagagta tcttagtgaa tgcttgctaa gcagttcaaa    1260
acaataccgg gcaatgatcg aagagcgcga cactactggt ggaaaagtga agggacaagg    1320 cactggaccl gttctcattg tgactcttgt tgatccagag acagaatcca gcatcaatgc    1380
tgccatgctc gaggaagggc ttgcccgact tgaaaggggc aagagatggg acaccaagga    1440
gaggaagaca gctctcgaga atctggaaca gttccaggag aaggcgaaga aggaaaggct    1500
gcggctgtgg cagtatggag acgtcgaatc tgacgaggaa gatcaagctc caggcgggag    1560 gagaccccg ccgcgtcggt agacgagata atgccgcggc aagcagtggc gcagtcatgg    1620 nttaaa                                                               1626
```

<210> SEQ ID NO 8
<211> LENGTH: 526
<212> TYPE: PRT
<213> ORGANISM: Triticum aestivum

<400> SEQUENCE: 8

```
His Glu Gly Gln Asn Ala Val Pro Val Met Asn Ser Ala Asp Thr Arg
  1               5                  10                  15

Val Leu Asp Tyr Gly Ser Val Phe Leu Gly Ser Pro Ser Pro Ala Asp
             20                  25                  30

Gly Asp Asp Thr Ser Ser Ala Pro Ser Thr Gly Thr Gln Pro Lys Ile
         35                  40                  45

Asn Val Ala Glu Leu Leu Leu Ser Arg Gly Phe Ala Glu Ile Ser Lys
     50                  55                  60

His Arg Asp Tyr Glu Glu Arg Ser His Tyr Phe Asp Ala Leu Leu Ala
 65                  70                  75                  80

Ala His Ser Arg Ala Glu Lys Ala Lys Gly Ile His Ser Asp Lys
                 85                  90                  95

Leu Pro Pro Val Met His Ile Thr Asp Leu Thr Met Val Asn Ser Lys
            100                 105                 110

Lys Ala Lys Asp Phe Leu Pro Phe Leu Gln Arg Asn Arg Arg His Thr
        115                 120                 125

Ala Val Val Glu Tyr Val Phe Ser Gly His Arg Phe Lys Leu Thr Ile
    130                 135                 140

Pro Lys Glu Thr Cys Ser Ile Ala Phe Ser Leu Ser Gly Val Arg Cys
145                 150                 155                 160

Pro Gly Lys Asp Glu Pro Tyr Ser Ser Glu Ala Ile Ala Leu Met Arg
                165                 170                 175

Arg Met Ile Leu Gln Arg Asp Val Glu Ile Glu Val Glu Thr Val Asp
            180                 185                 190

Arg Thr Gly Thr Phe Ile Gly Ser Leu Trp Glu Ser Lys Thr Asn Val
        195                 200                 205

Gly Ser Val Leu Glu Ser Gly Leu Gly Lys Leu Ser Ser Phe Gly
    210                 215                 220

Leu Asp Arg Ile Pro Asp Ala His Val Leu Thr Arg Ala Glu Lys Leu
225                 230                 235                 240

Ala Lys Gln Gln Lys Leu Lys Ile Trp Glu Asn Tyr Val Glu Gly Glu
                245                 250                 255

Glu Val Thr Asn Gly Ser Ala Ser Glu Ser Lys Gln Lys Glu Ile Leu
            260                 265                 270
```

-continued

```
Lys Val Val Ala Thr Glu Val Leu Gly Gly Lys Phe Tyr Ala Gln
            275                 280                 285

Thr Val Gly Asp Gln Arg Val Ala Ser Ile Gln Gln Gln Leu Ala Ser
        290                 295                 300

Leu Lys Leu Lys Glu Ala Pro Val Ile Gly Ala Phe Asn Pro Gly Lys
305                 310                 315                 320

Gly Glu Ile Val Leu Ala Gln Phe Ser Leu Asp Asn Ser Trp Asn Arg
                325                 330                 335

Ala Met Ile Val Asn Gly Pro Arg Gly Ala Val Glu Ser Val Asp Asp
            340                 345                 350

Lys Phe Glu Val Phe Tyr Ile Asp Phe Gly Asn Gln Glu Val Val Pro
        355                 360                 365

Tyr Asn Arg Ile Arg Pro Ala Asp Pro Ser Val Ser Ser Pro Pro
    370                 375                 380

Leu Ala Gln Leu Cys Ser Leu Ala Phe Ile Lys Val Pro Gly Leu Glu
385                 390                 395                 400

Asp Asp Asn Gly Gln Glu Ala Ala Glu Tyr Leu Ser Glu Cys Leu Leu
                405                 410                 415

Ser Ser Ser Lys Gln Tyr Arg Ala Met Ile Glu Glu Arg Asp Thr Thr
            420                 425                 430

Gly Gly Lys Val Lys Gly Gln Gly Thr Gly Pro Val Leu Ile Val Thr
        435                 440                 445

Leu Val Asp Pro Glu Thr Glu Ser Ser Ile Asn Ala Ala Met Leu Glu
450                 455                 460

Glu Gly Leu Ala Arg Leu Glu Arg Gly Lys Arg Trp Asp Thr Lys Glu
465                 470                 475                 480

Arg Lys Thr Ala Leu Glu Asn Leu Glu Gln Phe Gln Glu Lys Ala Lys
                485                 490                 495

Lys Glu Arg Leu Arg Leu Trp Gln Tyr Gly Asp Val Glu Ser Asp Glu
            500                 505                 510

Glu Asp Gln Ala Pro Gly Gly Arg Arg Pro Pro Arg Arg
        515                 520                 525

<210> SEQ ID NO 9
<211> LENGTH: 885
<212> TYPE: PRT
<213> ORGANISM: Homo sapiens

<400> SEQUENCE: 9

Met Val Leu Ser Gly Cys Ala Ile Ile Val Arg Gly Gln Pro Arg Gly
  1               5                  10                  15

Gly Pro Pro Glu Arg Gln Ile Asn Leu Ser Asn Ile Arg Ala Gly
            20                  25                  30

Asn Leu Ala Arg Arg Ala Ala Thr Gln Pro Asp Ala Lys Asp Thr
        35                  40                  45

Pro Asp Glu Pro Trp Ala Phe Pro Ala Arg Glu Phe Leu Arg Lys Lys
     50                  55                  60

Leu Ile Gly Lys Glu Val Cys Phe Thr Ile Glu Asn Lys Thr Pro Gln
 65                  70                  75                  80

Gly Arg Glu Tyr Gly Met Ile Tyr Leu Gly Lys Asp Thr Asn Gly Glu
                85                  90                  95

Asn Ile Ala Glu Ser Leu Val Ala Glu Gly Leu Ala Thr Arg Arg Glu
            100                 105                 110

Gly Met Arg Ala Asn Asn Pro Glu Gln Asn Arg Leu Ser Glu Cys Glu
        115                 120                 125
```

-continued

```
Glu Gln Ala Lys Ala Ala Lys Lys Gly Met Trp Ser Glu Gly Asn Gly
    130                 135                 140

Ser His Thr Ile Arg Asp Leu Lys Tyr Thr Ile Glu Asn Pro Arg His
145                 150                 155                 160

Phe Val Asp Ser His His Gln Lys Pro Val Asn Ala Ile Ile Glu His
                165                 170                 175

Val Arg Asp Gly Ser Val Val Arg Ala Leu Leu Leu Pro Asp Tyr Tyr
            180                 185                 190

Leu Val Thr Val Met Leu Ser Gly Ile Lys Cys Pro Thr Phe Arg Arg
        195                 200                 205

Glu Ala Asp Gly Ser Glu Thr Pro Glu Pro Phe Ala Glu Ala Lys
    210                 215                 220

Phe Phe Thr Glu Ser Arg Leu Leu Gln Arg Asp Val Gln Ile Ile Leu
225                 230                 235                 240

Glu Ser Cys His Asn Gln Asn Ile Val Gly Thr Ile Leu His Pro Asn
                245                 250                 255

Gly Asn Ile Thr Glu Leu Leu Leu Lys Glu Gly Phe Ala Arg Cys Val
            260                 265                 270

Asp Trp Ser Ile Ala Val Tyr Thr Arg Gly Ala Glu Lys Leu Arg Ala
        275                 280                 285

Ala Glu Arg Phe Ala Lys Glu Arg Arg Leu Arg Ile Trp Arg Asp Tyr
    290                 295                 300

Val Ala Pro Thr Ala Asn Leu Asp Gln Lys Asp Lys Gln Phe Val Ala
305                 310                 315                 320

Lys Val Met Gln Val Leu Asn Ala Asp Ala Ile Val Val Lys Leu Asn
                325                 330                 335

Ser Gly Asp Tyr Lys Thr Ile His Leu Ser Ser Ile Arg Pro Pro Arg
            340                 345                 350

Leu Glu Gly Glu Asn Thr Gln Asp Lys Asn Lys Lys Leu Arg Pro Leu
        355                 360                 365

Tyr Asp Ile Pro Tyr Met Phe Glu Ala Arg Glu Phe Leu Arg Lys Lys
    370                 375                 380

Leu Ile Gly Lys Lys Val Asn Val Thr Val Asp Tyr Ile Arg Pro Ala
385                 390                 395                 400

Ser Pro Ala Thr Glu Thr Val Pro Ala Phe Ser Glu Arg Thr Cys Ala
                405                 410                 415

Thr Val Thr Ile Gly Gly Ile Asn Ile Ala Glu Ala Leu Val Ser Lys
            420                 425                 430

Gly Leu Ala Thr Val Ile Arg Tyr Arg Gln Asp Asp Gln Arg Ser
        435                 440                 445

Ser His Tyr Asp Glu Leu Leu Ala Ala Glu Ala Arg Ala Ile Lys Asn
    450                 455                 460

Gly Lys Gly Leu His Ser Lys Lys Glu Val Pro Ile His Arg Val Ala
465                 470                 475                 480

Asp Ile Ser Gly Asp Thr Gln Lys Ala Lys Gln Phe Leu Pro Phe Leu
                485                 490                 495

Gln Arg Ala Gly Arg Ser Glu Ala Val Val Glu Tyr Val Phe Ser Gly
            500                 505                 510

Ser Arg Leu Lys Leu Tyr Leu Pro Lys Glu Thr Cys Leu Ile Thr Phe
        515                 520                 525

Leu Leu Ala Gly Ile Glu Cys Pro Arg Gly Ala Arg Asn Leu Pro Gly
    530                 535                 540
```

-continued

```
Leu Val Gln Glu Gly Glu Pro Phe Ser Glu Glu Ala Thr Leu Phe Thr
545                 550                 555                 560

Lys Glu Leu Val Leu Gln Arg Glu Val Glu Val Glu Val Glu Ser Met
                565                 570                 575

Asp Lys Ala Gly Asn Phe Ile Gly Trp Leu His Ile Asp Gly Ala Asn
            580                 585                 590

Leu Ser Val Leu Leu Val Glu His Ala Leu Ser Lys Val His Phe Thr
        595                 600                 605

Ala Glu Arg Ser Ser Tyr Tyr Lys Ser Leu Leu Ser Ala Glu Glu Ala
    610                 615                 620

Ala Lys Gln Lys Lys Glu Lys Val Trp Ala His Tyr Glu Glu Gln Pro
625                 630                 635                 640

Val Glu Glu Val Met Pro Val Leu Glu Glu Lys Glu Arg Ser Ala Ser
                645                 650                 655

Tyr Lys Pro Val Phe Val Thr Glu Ile Thr Asp Asp Leu His Phe Tyr
            660                 665                 670

Val Gln Asp Val Glu Thr Gly Thr Gln Phe Gln Lys Leu Met Glu Asn
        675                 680                 685

Met Arg Asn Asp Ile Ala Ser His Pro Pro Val Glu Gly Ser Tyr Ala
    690                 695                 700

Pro Arg Arg Gly Glu Phe Cys Ile Ala Lys Phe Val Asp Gly Glu Trp
705                 710                 715                 720

Tyr Arg Ala Arg Val Glu Lys Val Glu Ser Pro Ala Lys Ile His Val
                725                 730                 735

Phe Tyr Ile Asp Tyr Gly Asn Arg Glu Val Leu Pro Ser Thr Arg Leu
            740                 745                 750

Gly Thr Leu Ser Pro Ala Phe Ser Thr Arg Val Leu Pro Ala Gln Ala
        755                 760                 765

Thr Glu Tyr Ala Phe Ala Phe Ile Gln Val Pro Gln Asp Asp Asp Ala
    770                 775                 780

Arg Thr Asp Ala Val Asp Ser Val Val Arg Asp Ile Gln Asn Thr Gln
785                 790                 795                 800

Cys Leu Leu Asn Val Glu His Leu Ser Ala Gly Cys Pro His Val Thr
                805                 810                 815

Leu Gln Phe Ala Asp Ser Lys Gly Asp Val Gly Leu Gly Leu Val Lys
            820                 825                 830

Glu Gly Leu Val Met Val Glu Val Arg Lys Glu Lys Gln Phe Gln Lys
        835                 840                 845

Val Ile Thr Glu Tyr Leu Asn Ala Gln Glu Ser Ala Lys Ser Ala Arg
    850                 855                 860

Leu Asn Leu Trp Arg Tyr Gly Asp Phe Arg Ala Asp Asp Ala Asp Glu
865                 870                 875                 880

Phe Gly Tyr Ser Arg
                885

<210> SEQ ID NO 10
<211> LENGTH: 890
<212> TYPE: PRT
<213> ORGANISM: Ajellomyces capsulatus
<400> SEQUENCE: 10

Met Phe Arg Pro Arg Leu Arg Arg Glu Gly Asp Glu Val Lys Phe Asp
  1               5                  10                  15

Ile Ser Pro Gly Cys Pro Leu His Gly Phe Pro Val Ser Gly Ser Ser
             20                  25                  30
```

-continued

```
Cys Pro Ser Ala Val Leu Asp Gly Ser Leu Leu Thr Ser Tyr Tyr Phe
         35                  40                  45

Ala Leu Thr Ala Gln Pro Phe Ala Phe Gln Ser Arg Glu Phe Leu Arg
         50                  55                  60

Glu Leu Leu Val Gly Lys Val Val Lys Phe Gln Val Asp Tyr Thr Val
 65                  70                  75                  80

Pro Thr Arg Asn Gly Asn Thr Met Ile Val Lys Leu His Asn Asn Gln
                 85                  90                  95

Glu Asn Leu Ala Glu Leu Cys Val Ala Glu Gly Trp Val Lys Val Arg
             100                 105                 110

Glu Asp Ala Gly Lys Arg Glu Glu Ser Glu Asp Ile Val Ala Thr Val
         115                 120                 125

Asp Lys Leu Arg Glu Leu Glu Asn Arg Ala Arg Ser Glu Ser Lys Gly
         130                 135                 140

Val Trp Ala Ser Thr Gly Gly Glu Leu Glu Thr Ala Tyr Glu Val Pro
145                 150                 155                 160

Asp Pro Lys Ala Leu Ile Glu Ser Glu Lys Gly Asn Gln Ile Ala Ala
                 165                 170                 175

Val Val Glu Arg Val Leu Ser Gly Asp Arg Leu Ile Val Arg Leu Leu
             180                 185                 190

Val Ala Pro His Lys His Ile Gln Thr Leu Val Val Ala Gly Ile
         195                 200                 205

Arg Ala Pro Ala Thr Lys Arg Thr Asn Pro Asp Gly Thr Glu Gln Pro
         210                 215                 220

Gly Glu Pro Leu Gly Glu Gln Ala Gln Gln Phe Val Glu Leu Arg Leu
225                 230                 235                 240

Leu Gln Arg Lys Val Lys Ile Ser Leu Leu Gly Val Thr Pro Gln Asn
                 245                 250                 255

Gln Leu Val Ala Gly Val Leu His Pro Asn Gly Asn Ile Ala Lys Phe
             260                 265                 270

Leu Leu Glu Ala Gly Leu Ala Arg Cys Ala Asp His His Ser Thr Met
         275                 280                 285

Ile Gly Lys Asp Met Thr Thr Leu Arg Gln Ala Glu Asn Ala Ala Lys
         290                 295                 300

Glu Ala Arg Lys Gly Leu Phe Met Ser His Asn Ala Pro Lys Val Gly
305                 310                 315                 320

Ala Gly Ala Ala Gln Ala Asp Tyr Val Val Thr Arg Val Phe Ser Ala
                 325                 330                 335

Asp Thr Ile Phe Val Arg Thr Lys Thr Gly Lys Asp Glu Lys Arg Ile
             340                 345                 350

Ser Leu Ser Ser Val Arg His Pro Arg Thr Ser Asp Pro Lys Gln Ala
         355                 360                 365

Pro Phe Ile Leu Glu Ala Lys Glu Phe Met Arg Lys Lys Leu Ile Gly
         370                 375                 380

Lys His Val Lys Val Lys Ile Asp Gly Lys Arg Pro Ala Ser Glu Gly
385                 390                 395                 400

Tyr Glu Glu Arg Glu Val Gly Thr Val Met Ser Gly Asn Thr Asn Ile
                 405                 410                 415

Ala Leu Ala Leu Val Gln Ala Gly Tyr Ala Ser Val Ile Arg His Arg
             420                 425                 430

Arg Asp Asp Asp Arg Ser Pro Glu Tyr Asp Asp Leu Leu Arg Ala
         435                 440                 445
```

-continued

```
Glu Glu Ala Ala Gln Lys Glu Gly Lys Gly Met Trp Ser Ser Lys Pro
    450                 455                 460

Pro Thr Val Arg Ala Pro Gln Asp Tyr Ser Glu Asn Val Gln Lys Ala
465                 470                 475                 480

Lys Ile Gln Ala Ser Val Leu Gln Arg Gln Lys Val Pro Gly Val
                485                 490                 495

Val Asp Phe Val Lys Ser Gly Ser Arg Phe Thr Ile Leu Leu Pro Lys
            500                 505                 510

Asp Asn Ala Lys Leu Thr Leu Val Leu Ser Gly Ile Arg Ala Pro Arg
                515                 520                 525

Ser Ala Arg Asn Pro Gly Glu Thr Gly Glu Pro Phe Gly Gln Glu Ala
    530                 535                 540

His Asp Phe Ala Tyr Arg Arg Cys Met Gln Arg Asp Val Glu Ile Asp
545                 550                 555                 560

Val Glu Thr Ile Asp Lys Val Gly Gly Phe Ile Gly Ser Leu Tyr Ile
                565                 570                 575

Asn Arg Glu Ser Phe Ser Lys Ile Leu Val Glu Glu Gly Leu Ala Thr
            580                 585                 590

Val His Ala Tyr Ser Ala Glu Gln Gly Gly His Ala Ala Glu Leu Phe
    595                 600                 605

Ala Ala Glu Lys Lys Ala Lys Glu Ala Arg Lys Gly Leu Trp His Asp
610                 615                 620

Trp Asp Pro Ser Lys Asp Leu Glu Glu Gly Glu Thr Val Ala Thr Asn
625                 630                 635                 640

Gly Lys Asn Gly Ala Glu Ala Gly Ala Asp Ala Pro Gln Gln Arg Lys
                645                 650                 655

Lys Asp Tyr Arg Asp Val Met Val Thr Asn Val Asp Glu Asn Gly Lys
            660                 665                 670

Leu Lys Ile Gln Gln Ile Gly Ala Gly Thr Thr Ala Leu Thr Glu Met
        675                 680                 685

Met Ser Ala Phe Arg Ala Phe His Leu Asn Lys Ala Asn Asp Thr Ala
    690                 695                 700

Leu Ser Gly Pro Pro Lys Ala Gly Asp Leu Val Ala Ala Arg Phe Thr
705                 710                 715                 720

Glu Asp Asn Glu Trp Tyr Arg Ala Lys Ile Arg Arg Asn Asp Arg Glu
                725                 730                 735

Ala Lys Lys Ala Asp Val Val Tyr Ile Asp Tyr Gly Asn Ser Glu Thr
            740                 745                 750

Val Pro Trp Thr Arg Leu Arg Pro Leu Thr Gln Pro Gln Phe Ser Val
    755                 760                 765

Gln Lys Ile Arg Pro Gln Ala Thr Asp Thr Val Leu Ser Phe Leu Gln
770                 775                 780

Leu Pro Ala Ser Pro Glu Tyr Leu Arg Asp Ala Val Gly Tyr Leu Gly
785                 790                 795                 800

Glu Arg Thr Leu Asp Arg Gln Leu Val Ala Asn Val Asp Tyr Thr Ala
                805                 810                 815

Pro Asp Gly Thr Leu His Val Thr Leu Met Asp Pro Ala Glu Ser Lys
            820                 825                 830

Ser Leu Glu His Ser Ile Asn Ala Asp Val Ile Ser Glu Gly Leu Ala
        835                 840                 845

Met Val Pro Arg Lys Leu Lys Glu Trp Glu Arg Ser Ser Thr Glu Thr
    850                 855                 860
```

```
-continued

Leu Ala His Leu Glu Lys Leu Glu Asn Glu Ala Lys Glu Gly Arg Lys
865                 870                 875                 880

Gly Met Trp Glu Tyr Gly Ala Thr Glu Asp
                885                 890
```